(12) United States Patent
Sumikawa et al.

(10) Patent No.: US 7,544,834 B2
(45) Date of Patent: Jun. 9, 2009

(54) METHODS FOR PRODUCING NATEGLINIDE B-TYPE CRYSTALS

(75) Inventors: Michito Sumikawa, Yokkaichi (JP); Makoto Maruo, Yokkaichi (JP); Kazuo Miyazaki, Yokkaichi (JP); Shigehiro Nishina, Yokkaichi (JP); Yukiko Matsuzawa, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/757,769

(22) Filed: Jun. 4, 2007

(65) Prior Publication Data

US 2007/0232829 A1 Oct. 4, 2007

Related U.S. Application Data

(63) Continuation of application No. 10/421,888, filed on Apr. 24, 2003, now abandoned, which is a continuation of application No. PCT/JP01/09293, filed on Oct. 23, 2001.

(30) Foreign Application Priority Data

Oct. 24, 2000 (JP) .............................. 2000-324375

(51) Int. Cl.
*C07C 229/00* (2006.01)
(52) U.S. Cl. .................. 562/450; 562/444; 562/445
(58) Field of Classification Search ................ 562/450, 562/444, 445
See application file for complete search history.

(56) References Cited

U.S. PATENT DOCUMENTS

| 5,463,116 | A | 10/1995 | Sumikawa et al. |
| 5,488,150 | A | 1/1996 | Sumikawa et al. |
| 6,844,008 | B2 | 1/2005 | Yabuki et al. |
| 2003/0021843 | A1 | 1/2003 | Makino et al. |
| 2003/0073729 | A1 | 4/2003 | Kitahara et al. |
| 2004/0014815 | A1 | 1/2004 | Ninomiya et al. |
| 2004/0024219 | A1 | 2/2004 | Sumikawa et al. |
| 2004/0030182 | A1 | 2/2004 | Takahashi et al. |
| 2005/0101672 | A1 | 5/2005 | Koguchi et al. |

FOREIGN PATENT DOCUMENTS

JP 63-54321 3/1988

OTHER PUBLICATIONS

U.S. Appl. No. 11/757,769, filed Jun. 4, 2007, Sumikawa et al.

*Primary Examiner*—Taylor Victor Oh
(74) *Attorney, Agent, or Firm*—Oblon, Spivak, McClelland, Maier & Neustadt, P.C.

(57) ABSTRACT

A method for producing B-type crystals of nateglinide substantially free of H-type crystals is provided, which comprises drying solvated wet crystals of nateglinide at a low temperature until no solvent remains and making a crystal conversion thereof. According to this method, B-type crystals of nateglinide can be produced at an industrial scale without allowing other forms of the crystalline polymorphism to coexist.

24 Claims, No Drawings

US 7,544,834 B2

METHODS FOR PRODUCING NATEGLINIDE B-TYPE CRYSTALS

CROSS-REFERENCE TO RELATED APPLICATIONS

The present application is a continuation of U.S. Ser. No. 10/421,888, filed on Apr. 24, 2003, which is continuation of PCT/JP01/09293, filed on Oct. 23, 2001, which claims priority to JP 2000-324375, filed on Oct. 24, 2000.

BACKGROUND OF THE INVENTION

The present invention relates to methods for producing nateglinide (its chemical name: N-(trans-4-isopropylcyclohexylcarbonyl)-D-phenylalanine) that is useful as a therapeutic agent for diabetes. More specifically, it relates to methods for producing nateglinide B-type crystals substantially free of H-type crystals.

It is known that nateglinide is useful as a therapeutic agent for diabetes because it effectively lowers blood glucose by oral administration (Japanese Patent Publication No. Hei 4-15221). In this connection, the crystallization has to be carefully conducted under precisely controlled conditions in order to separate H-type crystals and difficulty of such crystallization procedure was problematic (see Japanese Patent No. 2,508,949).

On the other hand, one of crystal polymorphs of nateglinide, B-type crystals, has an advantage in that the B-type crystals can be easily prepared by conducting the crystallization under cooling. However, there is a possibility in that the B-type crystals are transferred to the H-type crystals during the production stage. In fact, when nateglinide was prepared in industrial scale, it was found that H-type crystals were contaminated in the resulting B-type crystals. Regarding nateglinide to be used as a medicine, it is preferable that a contamination of crystal polymorphs be as small as possible. Since the single crystalline form is the best desired, a method for producing B-type crystals of nateglinide by which a pharmaceutical formulation containing the B-type crystal exclusively without allowing other forms of the crystalline polymorphs to coexist has been desired to be developed.

DISCLOSURE OF THE INVENTION

An object of the present invention is to provide methods for producing B-type crystals of nateglinide at an industrial scale without allowing other forms of the crystalline polymorphism to coexist.

In the course of the study for the purpose of an efficient utilization of B-type crystals of nateglinide, the present inventors have found that a single crystal form of nateglinide can be produced at an industrial scale by selecting the conditions of the manufacturing process of nateglinide, and thus the present invention has been completed on the basis of this finding.

That is, the present invention provides a method for producing B-type crystals of nateglinide substantially free of H-type crystals, which comprises drying solvated wet crystals of nateglinide at a low temperature until no solvent remains and making a crystal conversion thereof.

Preferably, the present invention provides a method for producing B-type crystals of nateglinide substantially free of H-type crystals, which comprises drying solvated materials containing nateglinide hydrates obtained by crystallizing out from a nateglinide-containing solution under cooling, at a temperature of 50° C. or lower until no solvent remains, and heating the resultant at a temperature of 60 to 110° C. to convert the crystal form of the resultant into B-type crystal.

BEST MODE FOR CARRYING OUT THE INVENTION

Examples of the solvated wet crystals of nateglinide employed in the present invention include solvates with an alcohol such as methanol, ethanol and isopropyl alcohol, an acetate such as methyl acetate and ethyl acetate, or water. The solvates with an alcohol or hydrate are usually used as the solvated wet crystals of nateglinide. In cases of the solvates with ethanol, for example, nateglinide is added to 60% ethanol aqueous solution so that the concentration of nateglinide becomes 5 wt %, dissolved at a temperature of around 30° C. and cooled down to 10° C. or lower to obtain the solvates.

Among these, it is preferable that the hydrates can be easily obtained by adding water to an alcohol solution, preferably ethanol solution, of nateglinide, cooling it to 10° C. or lower, thereby crystals are precipitated out, and separating the resulting crystals therefrom.

Solvated wet crystals obtained are dried until no solvent remains any longer. In this step, the temperature employed may vary depending on the type and the amount of a solvent associated with the crystals, and may usually be 60° C. or lower, preferably 50° C. or lower. While no lower limit of the temperature is specified, a temperature of 20° C. or higher is usually employed in an economical point of view. Usually, it is preferable that the drying be conducted under the reduced pressure, and the drying can be completed in a short time of period when the pressure is as reduced as industrially possible.

While the drying at a low temperature can be continued until substantially no solvent remains any longer, no complete absence of the solvent is required, and the solvent may be present in an amount of about 5% by weight since it will be lost also upon the crystal conversion.

The dried crystals obtained are converted into B-type crystals by heating at 60 to 110° C., preferably 70 to 110° C. Usually, the crystal conversion is preferably conducted for 0.5 to 48 hours, more preferably 1 to 24 hours.

H-type crystals contaminated in the B-type crystals can be analyzed with DSC. It is preferable that no H-type crystals be detected by analyzing B-type crystals of nateglinide with the DSC.

Rising of the drying temperature at an early stage causes no substantial problem when wet B-type crystals of nateglinide are dried at a small scale in a laboratory since the solvent after the separation of the crystals remains only in a small amount and the drier can rapidly reach the maximum reduced pressure. However, the B-type crystals free of H-type crystals can be produced according to methods of the present invention, even in a production at an industrial scale, for example, production of 5 Kg or more of the B-type crystals per one batch, in which the solvent remains in the crystals in a large amount after the separation from the liquid where the crystallization is conducted and the time period required for reaching the maximum reduced pressure is relatively long in the drying step.

The present invention is further demonstrated with reference to the following examples, which are not intended to restrict the invention.

EXAMPLE 1

24.5 kg of H-type crystals of nateglinide were added to 360 L of ethanol and dissolved by stirring at room temperature.

240 L of water was added thereto and cooled to 5° C. after ensuring the dissolution, and then the solution was subjected to aging at 5° C. for 1 hour. The thus-precipitated crystals were separated to obtain 43.0 kg of wet crystals. The crystals were dried on a rack drier at 45° C. for 24 hours (moisture content about 1 wt %) and further at 90° C. for 12 hours to make the crystal conversion to obtain 13.3 kg of dried crystals. The crystals were subjected to DSC, which revealed the presence of a peak specific to the B-type crystals (melting point: about 130° C.) without showing a peak specific to the H-type crystals (melting point: about 139° C.). Therefore, it is concluded that the resulting crystals are only B-type crystals which are substantially free of the H-type crystals.

COMPARATIVE 1

37.0 kg of H-type crystals of nateglinide were added to 540 L of ethanol and dissolved by stirring at room temperature. 360 L of water was added thereto and cooled to 5° C. after ensuring the dissolution, and then the solution was subjected to aging at 5° C. for 1 hour. The thus-precipitated crystals were separated to obtain 46.7 kg of wet crystals. The crystals were dried with a conical drier at 30° C. for 3 hours (moisture content about 10 wt %) and further at 90° C. for 12 hours to make the crystal conversion to obtain 25.9 kg of dried crystals. The crystals were subjected to DSC, which showed peaks specific to the H-type crystals in addition to the B-type crystals.

COMPARATIVE 2

37.0 kg of H-type crystals of nateglinide were added to 540 L of ethanol and dissolved by stirring at room temperature. 360 L of water was added thereto and cooled to 5° C. after ensuring the dissolution, and then the solution was subjected to aging at 5° C. for 1 hour. The thus-precipitated crystals were separated to obtain 44.5 kg of wet crystals. The crystals were dried with a conical drier at 30° C. for 3 hours (moisture content about 10 wt %) and further at 90° C. for 15 hours to make the crystal conversion to obtain 26.6 kg of dried B-type crystals. The crystals were subjected to DSC, which showed peaks specific to the H-type crystals in addition to the B-type crystals.

By employing the conditions according to the invention, B-type crystals of nateglinide can be produced at an industrial scale without allowing other crystal forms to be present, and a pharmaceutical formulation containing B-type crystals of nateglinide as a single nateglinide crystal can be provided at a low cost.

What is claimed is:

1. A method for producing B-type crystals of nateglinide substantially free of H-type crystals, which comprises drying solvated wet crystals of nateglinide at a temperature of 50° C. or lower until 5% by weight or less of solvent remains and making a crystal conversion thereof by heating the resultant at 60 to 110° C.

2. The method of claim 1, wherein the resulting B-type crystals of nateglinide are crystals wherein H-type crystals are not detected with DSC.

3. The method of claim 1, wherein the drying is conducted until no solvent remains any longer.

4. The method of claim 1, wherein the solvated wet crystals are hydrates.

5. The method of claim 1, wherein said both steps for drying said solvated wet crystal of nateglinide at a low temperature and for the crystal conversion are conducted at an industrial scale.

6. The method of claim 1, wherein said solvated wet crystals is a solvate with an alcohol.

7. The method of claim 1, wherein said solvated wet crystals is a solvate with an acetate.

8. The method of claim 1, wherein said drying is at a temperature of 20° C. or greater.

9. The method of claim 1, wherein said heating is at a temperature of 70 to 110° C.

10. The method of claim 1, wherein said heating is for a time ranging from 0.5 to 48 hours.

11. The method of claim 1, wherein said heating is for a time ranging from 1 to 24 hours.

12. The method of claim 1, wherein said solvated wet crystals of nateglinide are solvated wet H-type crystals of nateglinide.

13. The method of claim 1, wherein prior to said drying H-type crystals of nateglinide are dissolved in ethanol at room temperature followed by precipitation of solvated wet crystals of nateglinide.

14. A method for producing B-type crystals of nateglinide substantially free of H-type crystals, which comprises drying solvated materials containing nateglinide hydrates obtained by crystallizing out from a nateglinide-containing solution under cooling, at a temperature of 50° C. or lower until 5% by weight or less of solvent remains, and heating the resultant at a temperature of 60 to 110° C. to convert the crystal form of the resultant into B-type crystal.

15. The method of claim 14, wherein the resulting B-type crystals of nateglinide are crystals wherein H-type crystals are not detected with DSC.

16. The method of claim 14, wherein said solvated wet crystals is a solvate with an alcohol.

17. The method of claim 14, wherein said solvated wet crystals is a solvate with an acetate.

18. The method of claim 14, wherein said solvated wet crystals are hydrates.

19. The method of claim 14, wherein said drying is at a temperature of 20° C. or greater.

20. The method of claim 14, wherein said heating is at a temperature of 70 to 110° C.

21. The method of claim 14, wherein said heating is for a time ranging from 0.5 to 48 hours.

22. The method of claim 14, wherein said heating is for a time ranging from 1 to 24 hours.

23. The method of claim 14, wherein said solvated wet crystals of nateglinide are solvated wet H-type crystals of nateglinide.

24. The method of claim 14, wherein prior to said drying H-type crystals of nateglinide are dissolved in ethanol at room temperature followed by precipitation of solvated wet crystals of nateglinide.

* * * * *